(12) United States Patent
Becker

(10) Patent No.: US 8,601,886 B2
(45) Date of Patent: Dec. 10, 2013

(54) APPARATUS FOR METALLIC PARTICULATE QUANTIFICATION

(76) Inventor: Andrew James Becker, Rosanna (AU)

(*) Notice: Subject to any disclaimer, the term of this patent is extended or adjusted under 35 U.S.C. 154(b) by 412 days.

(21) Appl. No.: 13/118,734

(22) Filed: May 31, 2011

(65) Prior Publication Data

US 2012/0304740 A1 Dec. 6, 2012

(51) Int. Cl.
*G01N 1/22* (2006.01)
*G01N 37/00* (2006.01)

(52) U.S. Cl.
USPC ........................................ 73/863.21; 73/28.01

(58) Field of Classification Search
USPC ............ 73/28.01, 28.04, 28.05, 31.07, 61.42, 73/863.21, 863.22
See application file for complete search history.

(56) References Cited

U.S. PATENT DOCUMENTS 3,748,576 A * 7/1973 Sigournay ................... 73/861.04
7,574,930 B2 * 8/2009 Bunker ....................... 73/864.33

OTHER PUBLICATIONS

Becker, "A Method for Rapidly Quantifying Filter Patch Wear Debris", COMADEM 2010 conference publication Jun. 28-Jul. 2, 2010—4 pages.
GASTOPS, "FilterCHECK, At-Line Filter Debris Analysis, FC290 System", online publication at www.gastops.com, accessed on Mar. 28, 2011—2 pages.
GASTOPS, "FilterCHECK, At-Line Filter Debris Analysis, FC400 System", online publication at www.gastops.com, accessed on Mar. 28, 2011—2 pages.
GASTOPS, "MetalSCAN, On-line Oil Debris Monitor, MetalSCAN Specification", online publication at www.gastops.com, accessed on Mar. 28, 2011—1 page.
GASTOPS, "MetalSCAN, Application Description", online publication at www.gastops.com, accessed on Mar. 28, 2011—5 pages.

* cited by examiner

*Primary Examiner* — Hezron E Williams
*Assistant Examiner* — Nathaniel Kolb
(74) *Attorney, Agent, or Firm* — Hamre, Schumann, Mueller & Larson, P.C.

(57) ABSTRACT

Some embodiments relate to an apparatus for metallic particulate detection. The apparatus comprises: an entry stage defining an input chamber to receive an element having particulate matter thereon; a sensor defining a passage in fluid communication with the input chamber to receive the particulate matter from the input chamber and to detect the particles in the particulate matter; a vented recovery stage defining a recovery chamber to receive and capture at least some of the particulate matter passing through the passage; and at least one air outlet positioned in the input chamber to direct pressurized air from the at least one air outlet to impinge on the element to remove the particulate matter from the element.

20 Claims, 18 Drawing Sheets

FIG. 12C  FIG. 12B

APPARATUS FOR METALLIC PARTICULATE QUANTIFICATION

TECHNICAL FIELD

Described embodiments relate generally to apparatus for metallic particulate detection and quantification and to systems for metallic particulate quantification that include such apparatus.

BACKGROUND

Machinery, such as aircraft machinery, can generate debris as a function of wear of the machinery components during operation. Where the debris is relatively large, this can provide an indication of the possible failure of the machinery. Extraction of wear debris from a lubrication system filter can be an effective tool for the identification of incipient failure of oil-wetted components. Traditional wear debris analysis methods, such as Spectrometric oil Analysis, suffer from particle size limitations (i.e. they typically detect particles less than 8 microns), and fine filtration present in modern aircraft machinery further reduces the effectiveness of this limited technique. In some cases, an oil filter may be used to capture wear debris in order to obtain information about wear-related failure modes of the machinery. Extraction of debris from such filter elements can be cumbersome and rely heavily on manual extraction and visual inspection of debris, which can be error-prone and inaccurate. Similarly, ferromagnetic particles captured on magnetic chip detectors can be difficult to accurately quantify.

It is desired to address or ameliorate one or more shortcomings or disadvantages associated with existing techniques for quantifying wear debris in particulate form, or to at least provide a useful alternative thereto.

SUMMARY

Some embodiments relate to an apparatus for metallic particulate detection, comprising:
  an entry stage defining an input chamber to receive an element having particulate matter thereon;
  a sensor defining a passage in fluid communication with the input chamber to receive the particulate matter from the input chamber and to detect the particles in the particulate matter;
  a vented recovery stage defining a recovery chamber to receive and capture at least some of the particulate matter passing through the passage; and
  at least one air outlet positioned in the input chamber to direct pressurised air from the at least one air outlet to impinge on the element to remove the particulate matter from the element.

The apparatus (or a system comprising the apparatus) may further comprise a source of pressurised air coupled to the at least one air outlet. The apparatus (or a system comprising the apparatus) further comprise a filter to filter air from the pressurised air source.

The recovery stage may comprise a porous grate to allow venting of the air. A porous membrane (which may be a Whatman® Number 4 90 mm diameter filter paper, for example) may be positionable, in use of the apparatus, on the grate to retain the particulate matter in the recovery stage as the air is vented. The grate may be manually removable from the recovery stage. The grate may have a centrally located magnet to attract ferrous particulate. The recovery chamber may have a larger cross-sectional area than the passage. The recovery chamber may widen in a direction of travel of the air to compensate for the increased resistance to flow or back pressure offered by the porous membrane in the recovery chamber and hence avoid or minimise particulate being transported back up through the apparatus.

The apparatus may be sized to be supported by a retort stand. The at least one air outlet may comprise at least two air outlets. The sensor may be configured to detect particles of the particulate matter greater than or equal to about 100 microns.

The element may be or comprise a filter membrane. The entry stage may comprise a clamp to hold an edge of the filter membrane. The clamp may be movable within the input chamber to facilitate separation of particulate matter from the filter membrane.

The clamp may be rotatable between a first position and a second position. In the first position, the filter membrane may be generally horizontal and support any particulate matter thereon, and in the second position, the clamp may allow the filter membrane to be freely suspended within the input chamber. When the filter patch is in the second position, air emitted from the at least one air outlet is passed over the filter patch, causing an air-induced vibration of the filter membrane and thus liberating particulate formerly supported on it. Particles that liberate under gravity alone will also be recorded by the sensor.

In alternative embodiments to the element being a filter membrane, the element may comprise at least one magnet to attract ferro-magnetic matter. The at least one air outlet may comprise multiple air outlets each arranged to direct air toward the at least one magnet from a different direction. The at least one air outlet may further comprise a series of outlets arranged to provide an air curtain around at least part of the element. The input stage may have a wall defining an opening therein to receive a magnet support element to which the magnet is coupled.

The entry stage, the sensor and the output stage may be substantially co-axial.

Some embodiments relate to a metallic particulate quantisation system comprising:
  the apparatus of any one of the embodiments described herein; and
  a computer coupled to receive an output of the sensor and configured to detect a size and quantity of particles in the particulate matter passing through the sensor passage based on the sensor output.

BRIEF DESCRIPTION OF THE DRAWINGS

Embodiments are described in further detail below, by way of example only, or with reference to the accompanying drawings, in which:

FIG. 12B is a plan view of the top plate of FIG. 12A;

FIG. 12C is a side view of the top plate of FIG. 12B;

DETAILED DESCRIPTION

Figure 1:
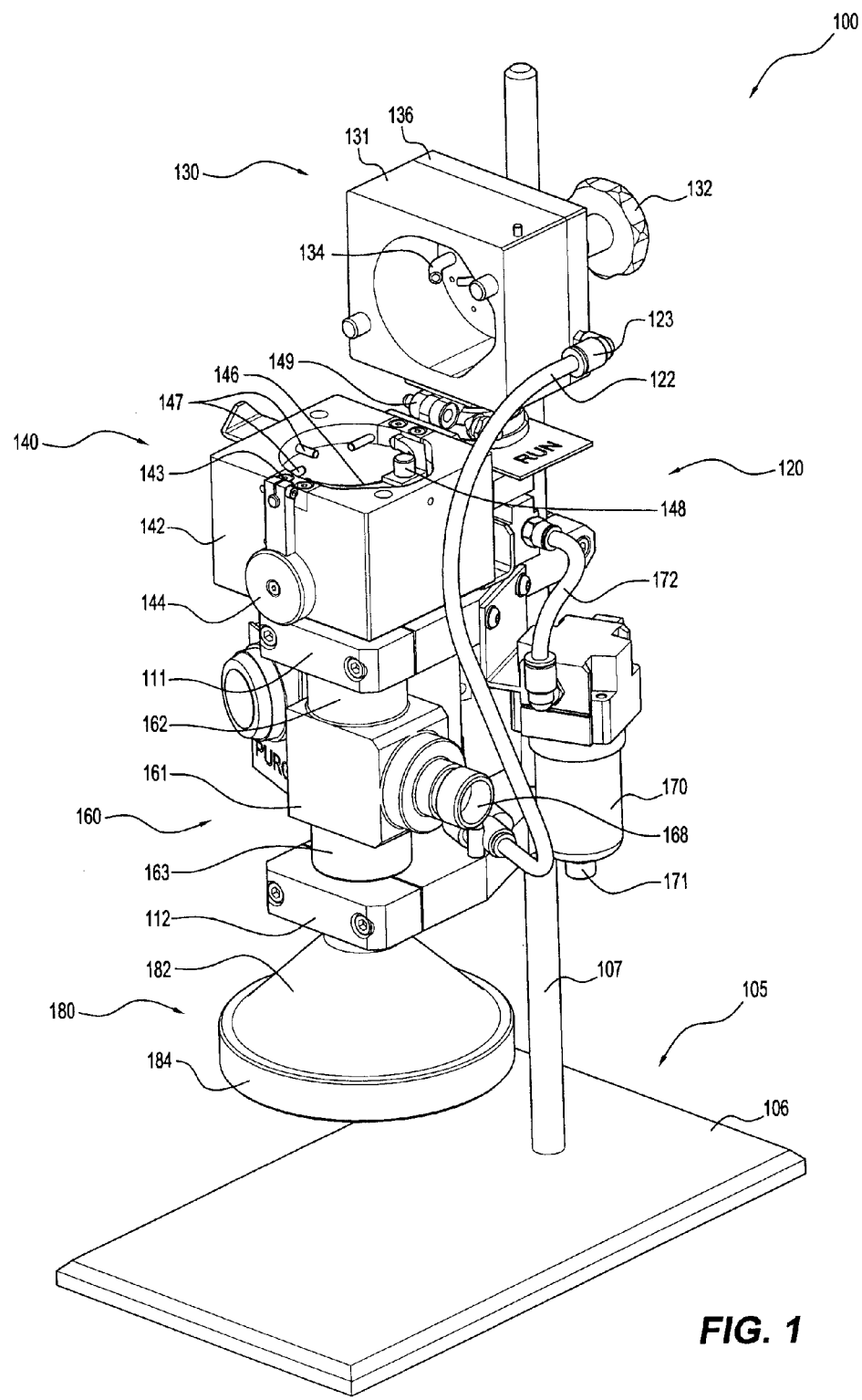
FIG. 1 is a perspective view of apparatus according to some embodiments for particulate detection.

Described embodiments relate generally to apparatus for metallic particulate detection and quantification and to systems for metallic particulate quantification that include such apparatus.

In the description and the drawings, like reference numerals are used to indicate like features and/or functions as between the drawings and among various embodiments.

Referring now to FIG. 1, there is shown an apparatus 100 for metallic particulate detection and quantification. Apparatus 100 comprises an entry stage 120, an inductive metallic particulate sensor 160 and a recovery stage 180 coupled together so that particulate matter introduced into entry stage 120 is passed through sensor 160 and into recovery stage 180 under the influence of air pressure and gravity. Apparatus 100 may comprise one or more clamps, such as upper and lower support clamps 111, 112 to support the apparatus 100 relative to some form of support means, such as a post 107 of a retort stand 105. Retort stand 105 has a base 106 to which the post 107 is fixedly coupled. As illustrated in FIG. 1 (and also FIG. 2), apparatus 100 is sized to be supportable by the retort stand 105 and can therefore be relatively portable and can be mounted or positioned easily on a desk or benchtop.

Entry stage 120 has an upper part 130 in order to provide an air supply and a lower part 140, which acts as a particulate receiver. The upper part 130 of entry stage 120 has a housing component 131 to which is fixedly coupled (by screws 138) a top plate 136. The upper part 130 is hingedly coupled to the lower part 140 by a hinge mechanism 149 (having mating hinge parts 149a, 149b) coupled to the lower part 140 and upper part 130, respectively.

The upper part 130 is movable between a closed position, in which the upper part 130 directly overlies and covers an upper surface 624 (FIG. 6) of lower part 140 and an interior chamber of the entry stage 120 is inaccessible, and an open position (as shown in FIG. 1), in which the lower part 140 is uncovered by the upper part 130 and the interior chamber of the entry stage 120 is accessible. Screw-threaded fasteners 132 extend through the upper part 130 for threaded engagement with apertures 622 (FIG. 6A) in the lower part 140 to retain the upper part 130 in the closed position during operation of the apparatus 100. The design of the hinge 149 and two screw-threaded fasteners 132 allows the upper part 130 and lower part 140 to effectively seal against each other and do not create a cavity that would allow particles to become entrapped and prevent them from being analysed.

Figure 3E:
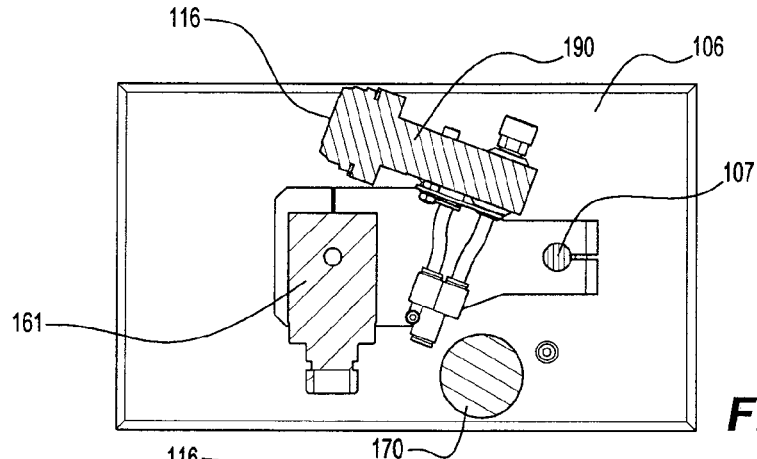
FIG. 3E is a cross-sectional plan view of part of the apparatus shown in FIG. 3A, taken along line B-B of FIG. 3A.
Figure 3B:
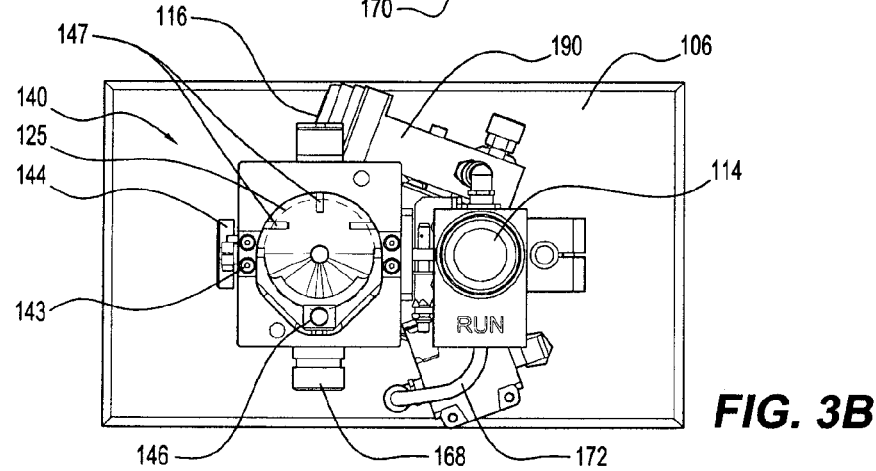
FIG. 3B is a plan view corresponding to the side view of FIG. 3A.
Figure 3A:
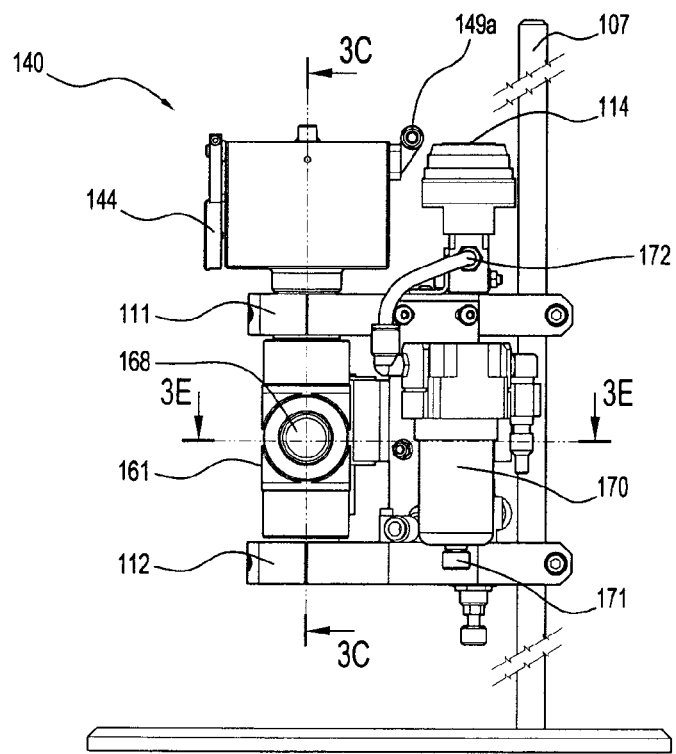
FIG. 3A is a side elevation of part of the apparatus of FIGS. 1 and 2.
Figure 3C:
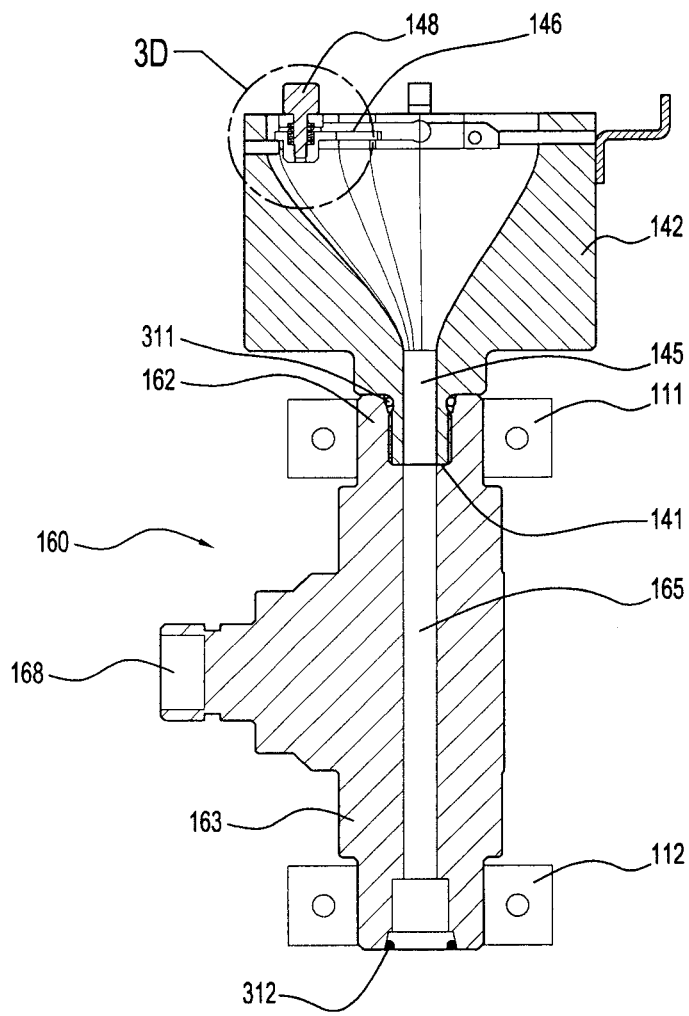
FIG. 3C is a side cross-section of the apparatus, taken along line A-A of FIG. 3A.
Figure 3D:
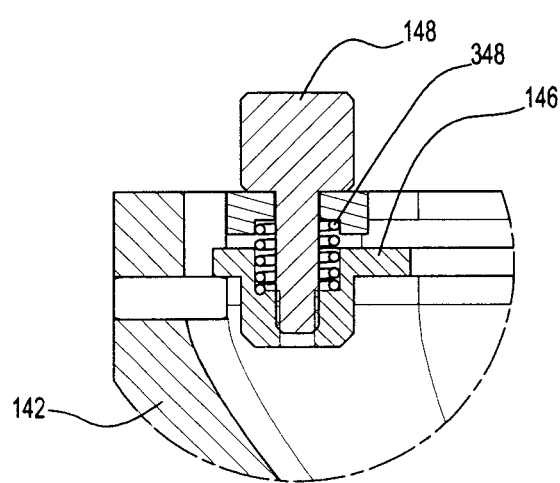
FIG. 3D is close up partial side cross-section of part of the apparatus shown in FIG. 3C, indicated by section C in FIG. 3C.

Top plate 136 defines an air supply passage therein for receiving pressurised air via an air supply conduit 122. Conduit 122 is coupled to top plate 136 by a rotatable fluid conduit coupling 123. An air supply nozzle 134 is coupled to part of top plate 136 in order to receive the pressurised air and direct it toward a filter membrane 125 (FIG. 3B), such as a filter patch positioned in the chamber when the upper part 130 is closed. Pressurised air emitted from the air nozzle 134 and impinging on the filter membrane 125 is intended to impinge on the filter membrane 125, causing air-induced vibration (flutter) that will dislodge or otherwise separate particulate matter (that was on the filter membrane 125 when it was inserted into the chamber) from the filter membrane 125 so that the particulate can pass through the sensor 160.

The membrane 125 may be a flexible filter patch having a pore size of around 60 to 80 microns, for example. The filter patch may be a nylon filter patch, such as is available from Millipore™. The filter membrane 125 is chosen to be able to hold particles of 100 microns or greater and to mostly allow smaller particles to be passed through. This is because particles smaller than about 100 microns are more numerous and of less interest in the analysis of wear debris than particles of 100 microns and greater. Cellulose filter membranes are generally not sufficiently robust enough to withstand the air-induced flutter.

Lower part 140 of entry stage 120 has a receiver body 142 that defines a lower part of input chamber 610, the upper part of which is defined by the hollow interior of housing component 131. The part of the input chamber 610 defined by receiver body 142 is somewhat funnel-shaped, although it is not perfectly circular in cross-section, at least near the chamber upper rim 626 (FIGS. 6A to 6E). This approximate funnel shape is defined by an inwardly sloping chamber wall surface 615 having a smooth, edgeless contour as it transitions in a downward direction toward a narrow outlet passage 145. Outlet passage 145 communicates with a central circular bore of inductive particulate sensor 160 defining a passage 165 through which the particulate must pass in order to be detected and quantified. The chambers and passages of the apparatus 100 through which the particulate matter passes or in which it may be temporarily retained are generally free of edges of ledges that would tend to hinder, trap or interrupt the downward passage of the particulate through the sensor 160 and into the recovery stage 180.

Figure 6A:
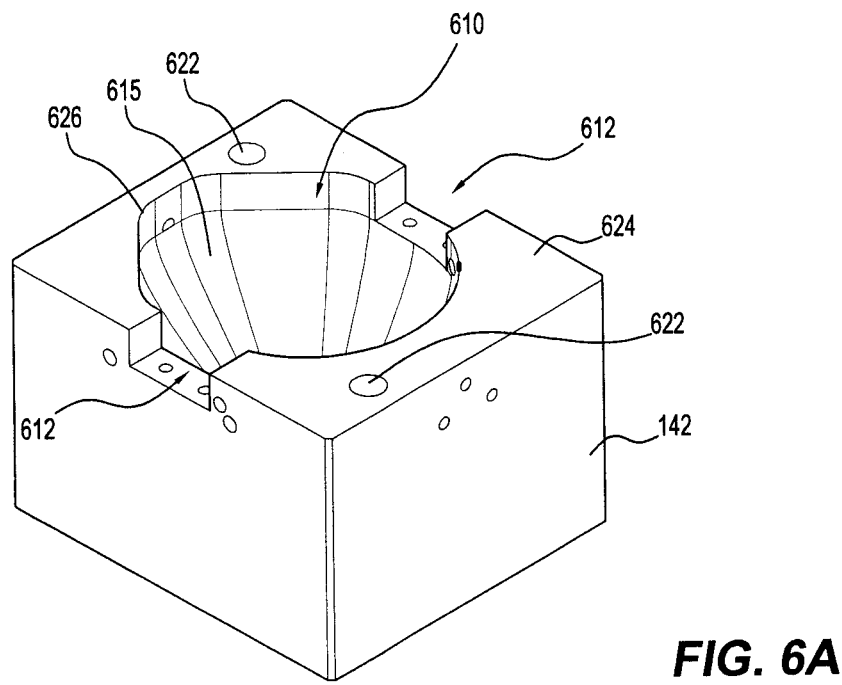
FIG. 6A is a top perspective view of a lower part of an entry stage of the apparatus of FIGS. 1 and 2.
Figure 6B:
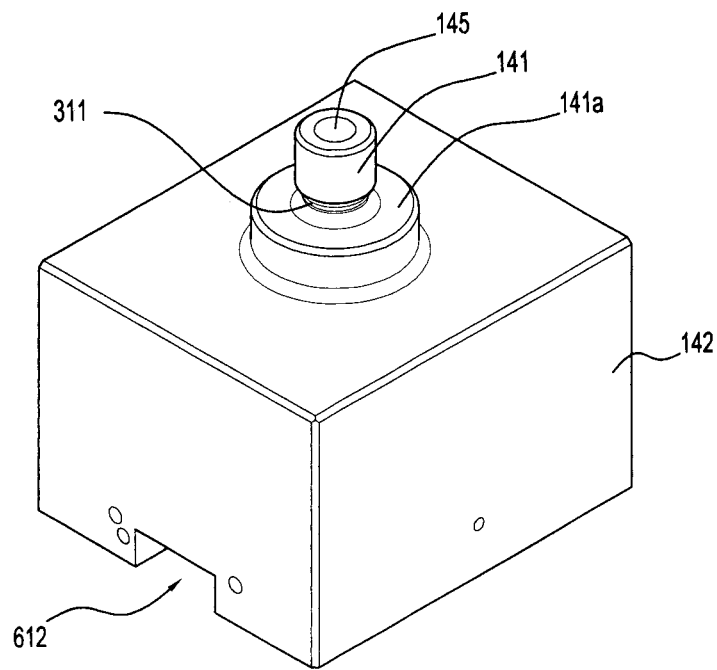
FIG. 6B is a perspective view of the lower part of the entry stage of FIG. 6A, shown inverted.
Figure 6E:
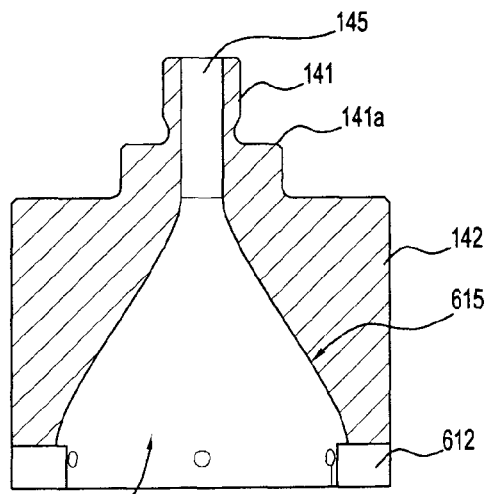
FIG. 6E is a further cross-sectional view of the lower part of the entry stage, taken along line B-B.
Figure 6C:
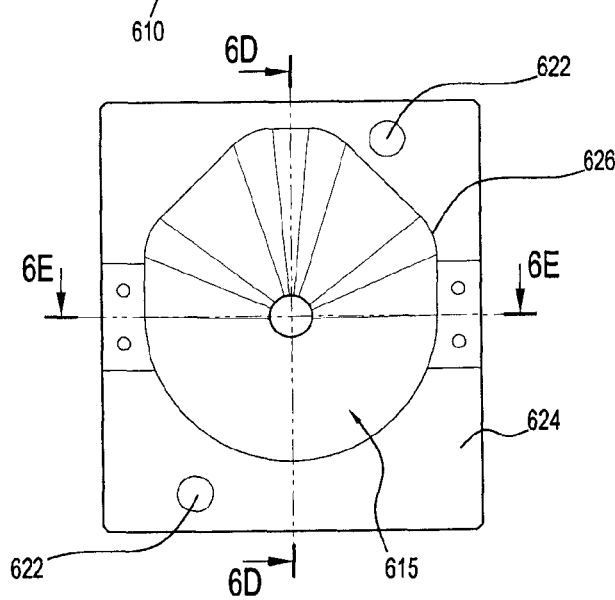
FIG. 6C is a plan view of the lower part of the entry stage.
Figure 6D:
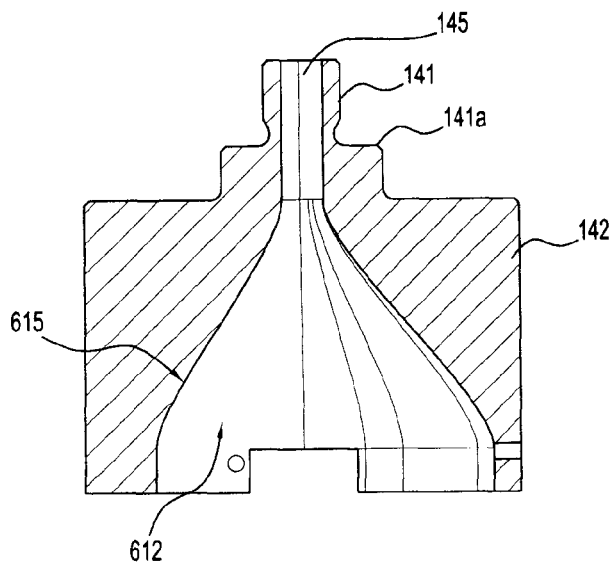
FIG. 6D is a cross-sectional view of the lower part of the entry stage, taken along line A-A of FIG. 6C.
Figure 7A:
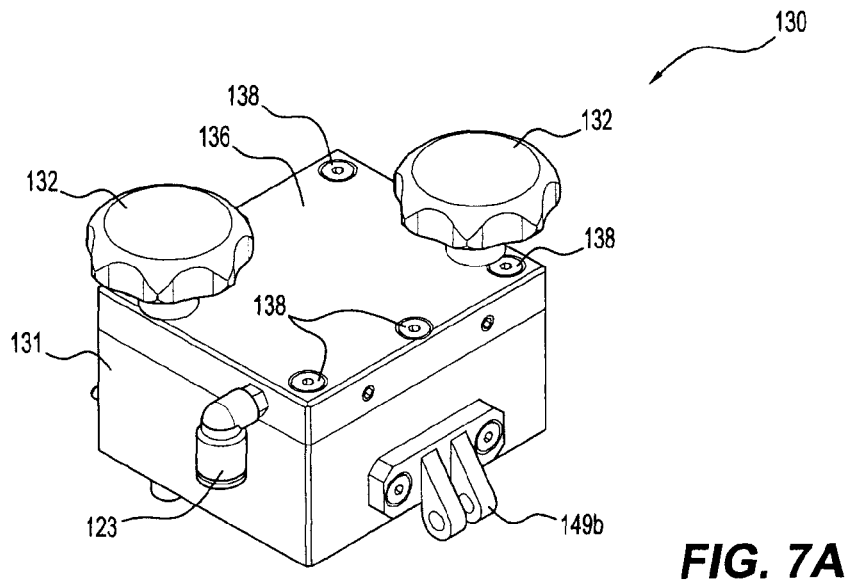
FIG. 7A is a top perspective view of an upper part of the entry stage of the apparatus of FIG. 1.
Figure 7B:
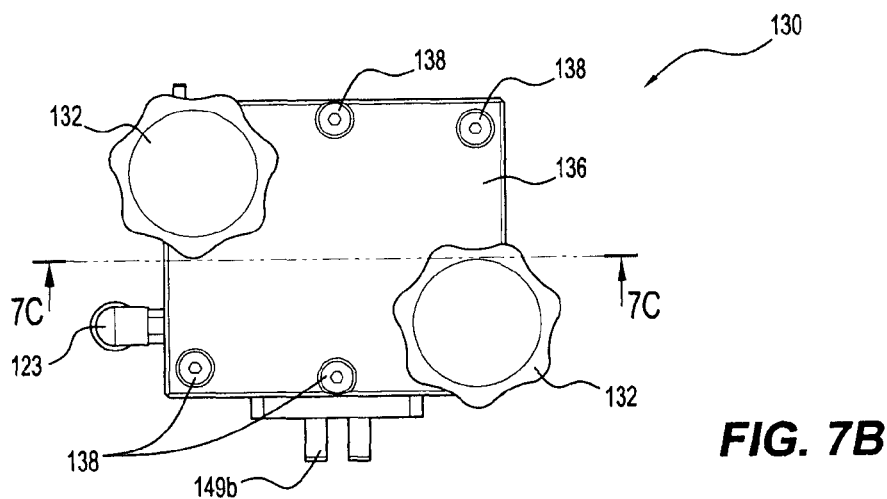
FIG. 7B is a plan view of the upper part of the entry stage shown in FIG. 7A.
Figure 7C:
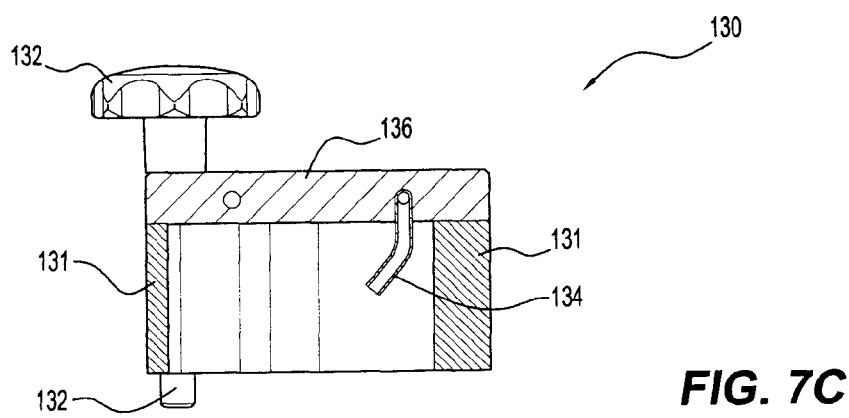
FIG. 7C is a side cross-sectional view of the upper part of the entry stage, taken along line B-B of FIG. 7B.

As illustrated in FIGS. 6A to 6B, receiver body 142 has a coupling nozzle 141 to be sealingly received in an inlet port 162 at an upper end of the sensor body 161. The sealing arrangement between receiving body 142 and sensor body 161 is aided by an inlet sealing member 311 arranged around the base of the coupling nozzle 141 and adjacent a sealing shoulder 141a of the receiver body 142. Other suitable sealing means may be used instead or in addition to inlet sealing member 311, which may comprise an O-ring, for example.

Figure 13A:
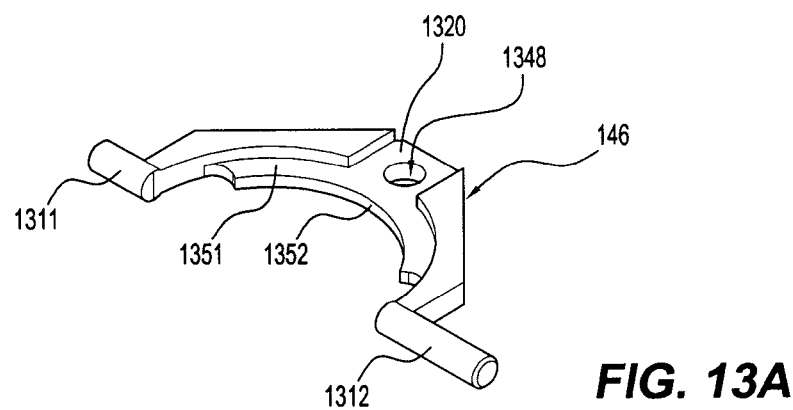
FIG. 13A is a perspective view of a movable clamp for use in a lower part of the entry stage of the apparatus shown in FIG. 1.
Figure 13C:
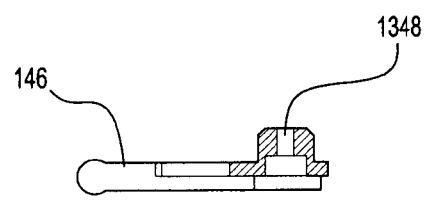
FIG. 13C is a side view of the clamp of FIG. 13A.
Figure 13B:
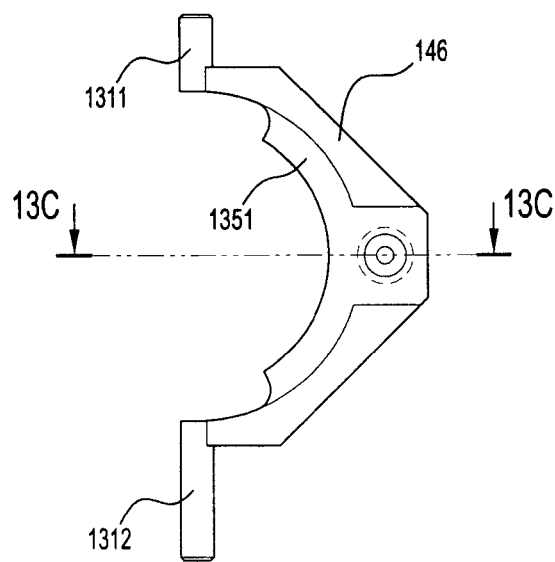
FIG. 13B is a plan view of the clamp of FIG. 13A.
Figure 13D:
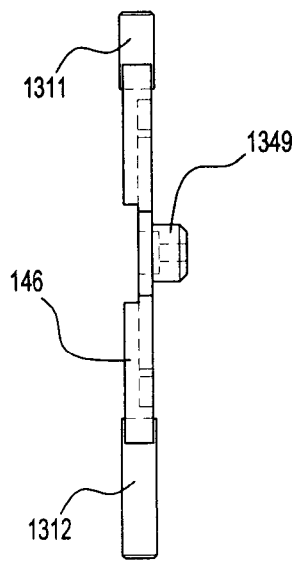
FIG. 13D is an end view of the clamp of FIG. 13A.

Receiver body 142 also defines opposed clamp seat positioning notches 612 to receive bearing seats 143 which support membrane clamp 146 in a freely rotatable manner. Membrane clamp 146 has a clamp screw 148 coupled to the membrane clamp 146 so as to be manually adjustable to clamp or unclamp a side edge of a filter membrane 125 when it is positioned to be supported by a support flange 1351 (FIGS. 13A to 13B) and membrane support pins 147 in a generally horizontal configuration. In this way, a filter membrane 125 having particulate matter thereon can be inserted adjacent the chamber upper rim 626 and clamped at one side edge thereof using clamp screw 148.

Membrane clamp 146 is approximately omega-shaped, having a first bearing arm 1311 rotatably supported by one of the bearing seats 143 and a longer second bearing arm 1312 rotatably supported by an opposite bearing seat 143. Membrane clamp 146 has a central body 1320 of a roughly concave profile, formed in part by a concave rim 1352, facing an axis of rotation extending through the first and second arms 1311, 1312. The first and second arms 1311, 1312 extend from lateral edges of the central body 1320. Integrally formed with or coupled to the central body 1320 is a fixed nut 1349, which together with the central body 1320 defines a clamp screw aperture 1348 for receiving clamp screw 148. A further small floating plate (not shown) may cooperate with the clamp screw 148 to assist in clamping an edge of the filter membrane 125 against support flange 1351.

Once the upper part 130 of entry stage 120 is closed and secured by screw-threaded fasteners 132, a membrane positioning lever 144, which is coupled to the second bearing arm 1312 of the membrane clamp 146, can be used to rotate the membrane 146 from a generally horizontal rest position to a generally vertical position, in which air from nozzle 134 can directly impinge on the filter membrane 125 freely suspended in the input chamber 610 in order to induce flutter of the filter membrane 125 and hence remove particulate matter from the filter membrane 125 so that it can pass into centre 160. As the membrane clamp 146 only clamps one side edge of the filter membrane 125, and this is rotated so that the clamped edge is uppermost when membrane positioning lever 144 is actuated, this allows an agitation of most of the body of the filter membrane 125 under the influence of the pressurised air from nozzle 134 to assist in removing as much particulate from the filter member 125 as possible.

Particulate removed from filter membrane 125 then passes through outlet passage 145 and along sensor passage 165, where an inductive element of sensor 160 senses the presence and approximate size of each passing particle. The sensor 160 may be an inductive wear debris sensor available from Gas-TOPS under the brand MetalSCAN™, for example or may be another suitable sensor that enables quantisation of metallic particulate passing therethrough.

Sensor 160 has an outlet port 163 for sealingly coupling to a coupling nozzle 186 of the recovery stage 180. An outlet sealing member 312, for example in the form of an O-ring or other sealing member, may be located around a base of the coupling nozzle 186 adjacent a shoulder 188 of the recovery stage 180. Alternatively, the outlet sealing member 312 may be provided on the inside of the outlet port 163. Shoulder 188 is arranged to abut the sensor body 161 adjacent the outlet port 163 to promote a stable sealing engagement therewith.

Figure 5A:
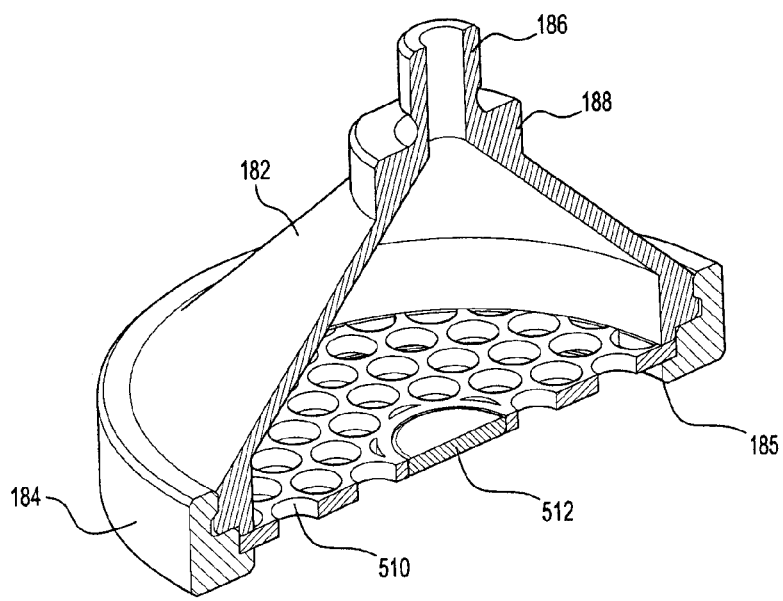
FIG. 5A is a perspective cutaway view of a recovery stage of the apparatus of FIGS. 1 and 2.
Figure 5B:
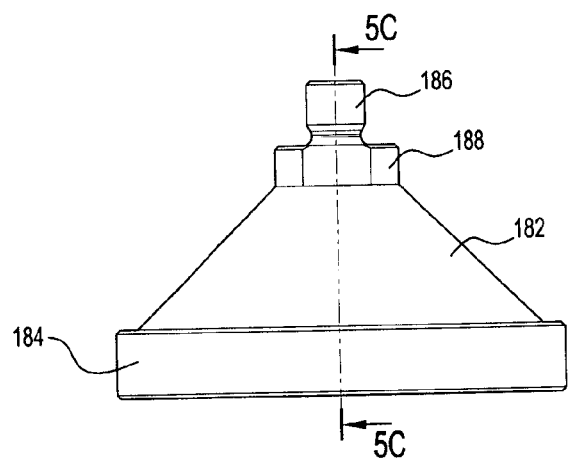
FIG. 5B is a side view of the recovery stage.
Figure 5C:
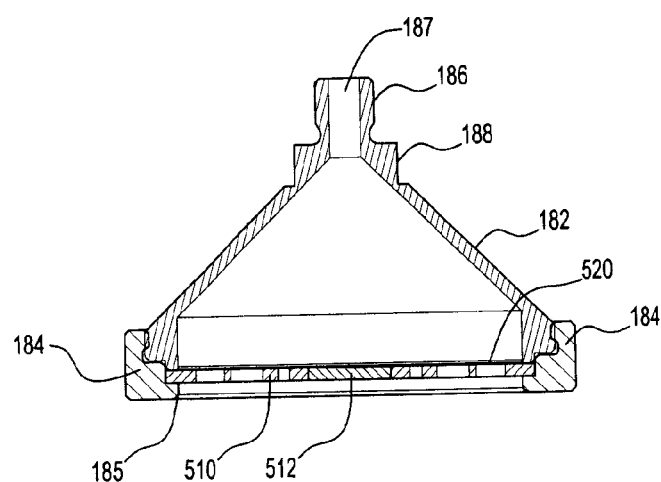
FIG. 5C is a cross-sectional view of the output stage, taken along line C-C of FIG. 5B.

Recovery stage 180 is shown in more detail in FIGS. 5A, 5B and 5C, where it can be seen that it has a generally conical body 182 that defines a recovery chamber that expands from adjacent a recovery passage 187 (that communicates with passage 165) to a substantially widened based region of the conical body 182. A recovery membrane 520 (FIG. 5C) is positioned just inside the outlet of the recovery stage 180. The expanding conical transition of conical body 182 enables a larger diameter recovery membrane 520 to be used, compared to the smaller diameter filter membrane 125. The recovery membrane 520 may be a Whatman® Number 4 filter paper having a porosity of 20 to 25 microns, for example. The broadening transition avoids excessive backpressure that would otherwise be caused by the finer grade recovery membrane 520, which may cause particles to be inadvertently redirected to places other than the recovery membrane 520. The larger diameter recovery membrane 520 also serves as a convenient indication that the particles have been processed by the instrument.

Although the body 182 of the recovery stage 180 is described and depicted as being conical, it need not be perfectly conical and could instead adopt other suitable forms, provided the recovery chamber expands in a direction of travel of air from the recovery passage 187 toward the bottom of a recovery stage 180 in a manner that avoids a disruptive amount of backpressure in the presence of the larger diameter recovery membrane 520.

Conical body 182 supports a recovery cap 184, for example by a screw-threaded engagement therebetween or another manually decoupleable engagement. Recovery cap 184 has a lower circumferential lip 185 arranged to support a generally disc-shaped grate 510 around a circumferential edge of the grate 510. When the recovery cap 184 is engaged with the base region of conical body 182, the grate 510 is held by the circumferential lip 185 against the base of the conical body 182.

Grate 510 is generally disc-shaped and porous, including multiple relatively large pores to allow air to easily escape therethrough from the recovery chamber. Grate 510 may support a central disc-shaped magnet 512 so as to be generally positioned in alignment with the central axis of the recovery passage 187 (as well as passages 165 and 145). When the recovery membrane 520 (i.e. a filter patch) is positioned over the grate 510 (and held in place between the base of conical body 182 and circumferential lip 185 of recovery cap 184), particulate entering the recovery chamber from the passages 165, 187 will generally be caught by the recovery membrane 520 instead of passing through grate 510. The recovery membrane 520 is selected to have a porosity smaller than the filter membrane 125 in order to ensure the capture of particles greater than or equal to around 100 microns. Particulate matter thus passed through the sensor 160 and deposited on recovery membrane 520 can then be further inspected and/or preserved by removal of the recovery cap 184.

Where magnet 512 is present in grate 510, ferromagnetic particulate within the particulate population passing through sensor 160 will be attracted to that part of the recovery membrane 520 that overlies the central part of the grate 510 and the magnet 512 in particular. Thus, where ferromagnetic particles are of particular interest, these can be separated from the other particles and further inspected and/or retained while the remainder of the particulate is discarded or transferred to a separate receptacle.

The arrangement of the entry stage 120, sensor 160 and recovery stage 180 of the apparatus 100 (and for apparatus 200) is generally vertically coaxial in order that particulate placed in the entry stage 120, once removed from the element 125 or 237 that carries it, can pass through the sensor 160 under the influence of gravity and air pressure.

Figure 14:
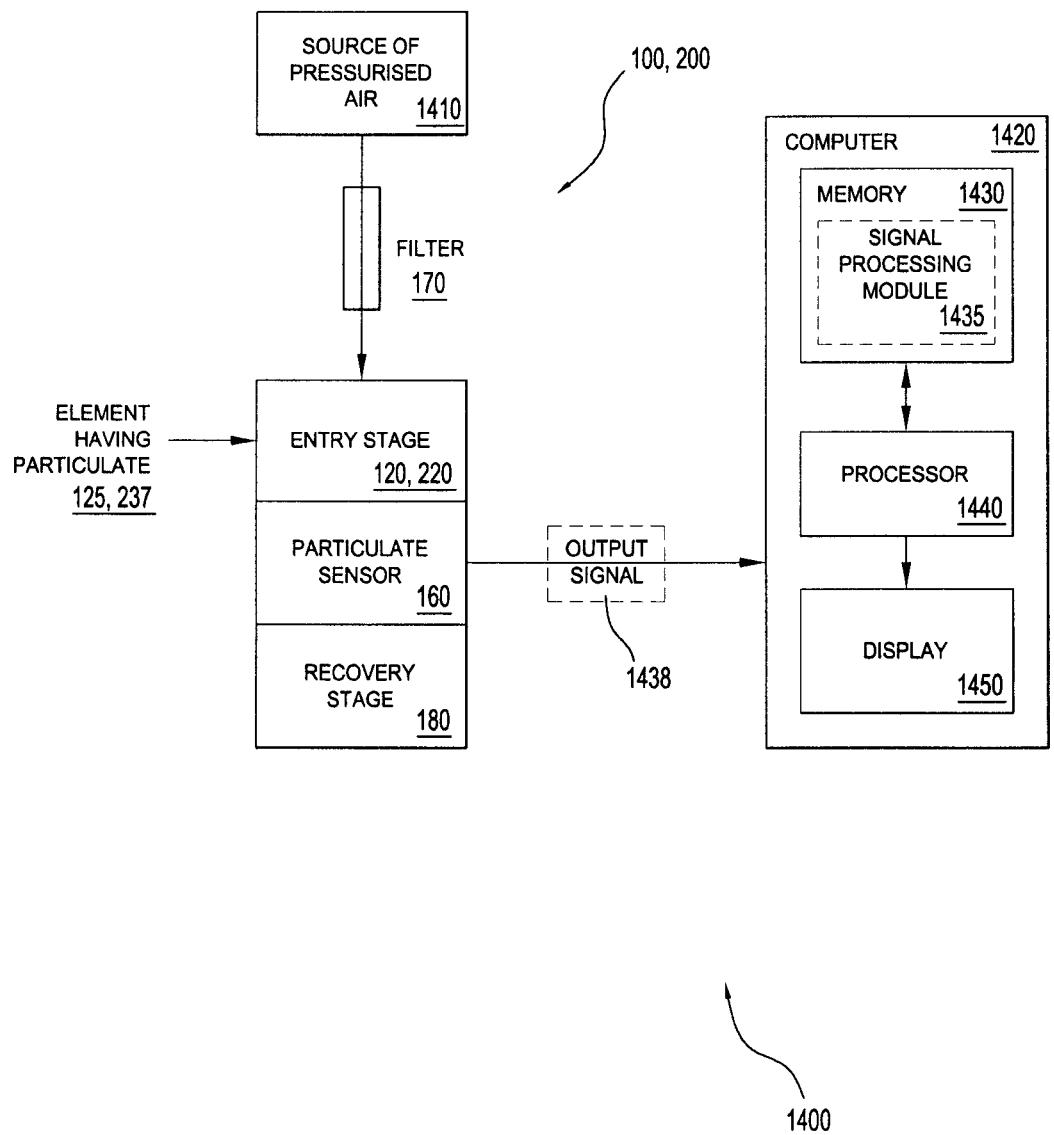
FIG. 14 is a block diagram of a particulate quantisation system including the apparatus of FIG. 1 or FIG. 2.

Apparatus 100 (and also apparatus 200) can be used as part of a system 1400 for particulate quantification, as shown in FIG. 14, where the system 1400 includes a source of pressurised air 1410 and a computer 1420. The computer 1420 is arranged to receive output signals from sensor coupling 168 of sensor 160 in order to quantify the particulate passing therethrough. The source of pressurised air 1410 is provided to an inlet 171 of an air filter 170 that is coupled via a fluid conduit 172 to an actuator 114 that acts as a "run" button that, when pressed, allows pressurised air to pass into the entry chamber 610 via the air delivery nozzle 134.

Figure 4:
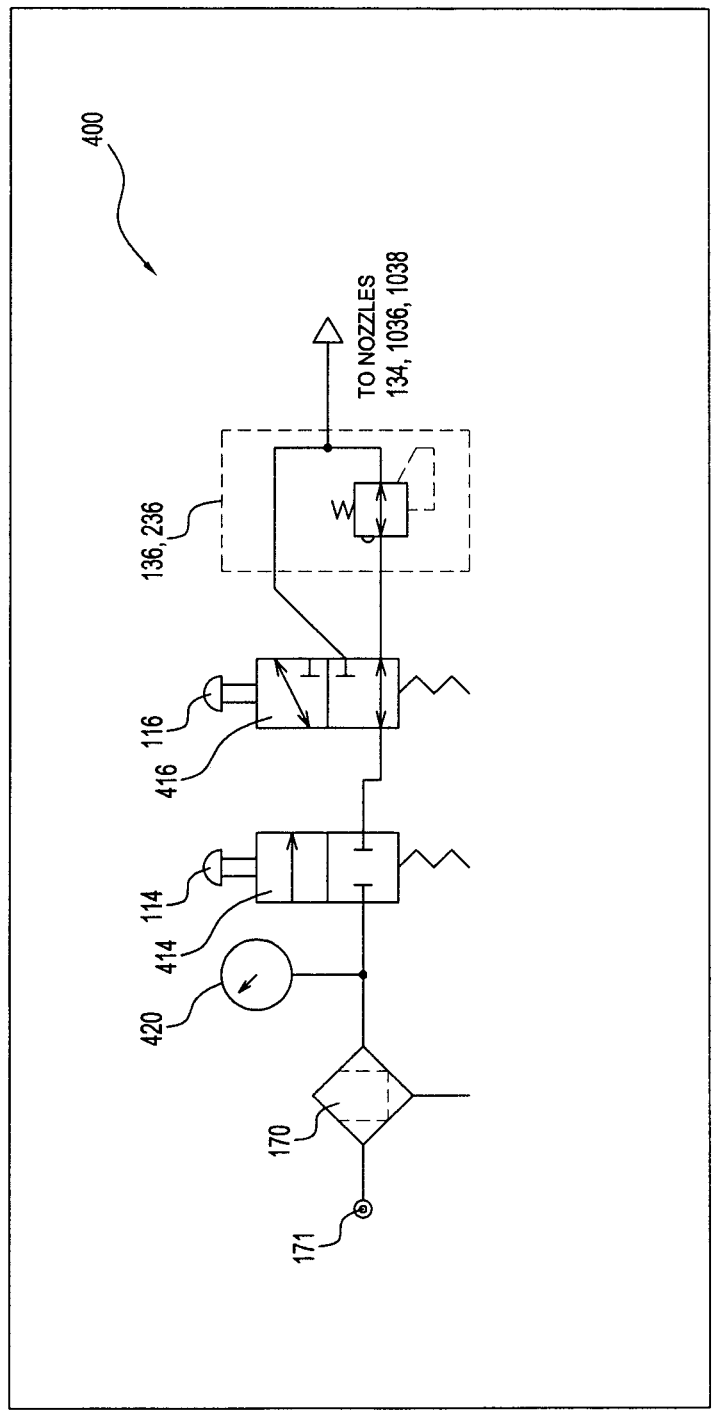
FIG. 4 is a diagram of pneumatic control components of the apparatus.

A diagram of pneumatic control components 400 is shown in further detail in FIG. 4. In addition to actuator 114, which causes a run valve 414 to open, a purge valve 416 may be provided in series with the run valve 414 and actuated by a second actuator "purge" 116. This purge valve 416 allows for additional flushing of the interior volumes and passages of apparatus 100, if desired. In some embodiments, the purge valve 416 may be omitted. A valve body 190 of purge valve 416 can be seen in FIGS. 3B and 3E. In some embodiments, a pressure gauge 420 may be coupled to the fluid supply line in order that the user of the apparatus 100 can check that pressure levels within the apparatus 100 or 200 are appropriate.

Referring again to FIG. 14, apparatus 100 (and also apparatus 200) is intended to be used with a computer 1420, which may be any suitable type of computing device, having a processor 1440, a memory 1430 and a display 1450. The memory 1430 stores processor-executable program code to implement a signal processing module 1435 specifically configured to process the received output signals from particulate sensor 160 in order to determine the number and size of the particles passing through the sensor 160. The processor 1440 executes the signal processing module 1435 and causes the display 1450 to generate a computerised display indicating the number and size of particles detected. For example, the display may show the number of particles detected within each of a series of consecutive size ranges. Thus, the display may show how many particles were detected within the size range of 800 microns to 1000 microns, how many were detected in the range of 600 microns to 800 microns, and so on, down to a lower limit of around 100 microns.

Some embodiments, a signal processing component 1438 may be used intermediate the sensor 160 and the computer 1420 to provide analogue-to-digital signal conversion, initial processing and/or control functions in relation to sensor 160. In such embodiments, the signal processing module 1435 is responsive to output signals from the signal processing component 1438 and generates the display output (results) to the computer 1420 for display. The computer is used to change settings in the signal processing box if required.

Figure 8:
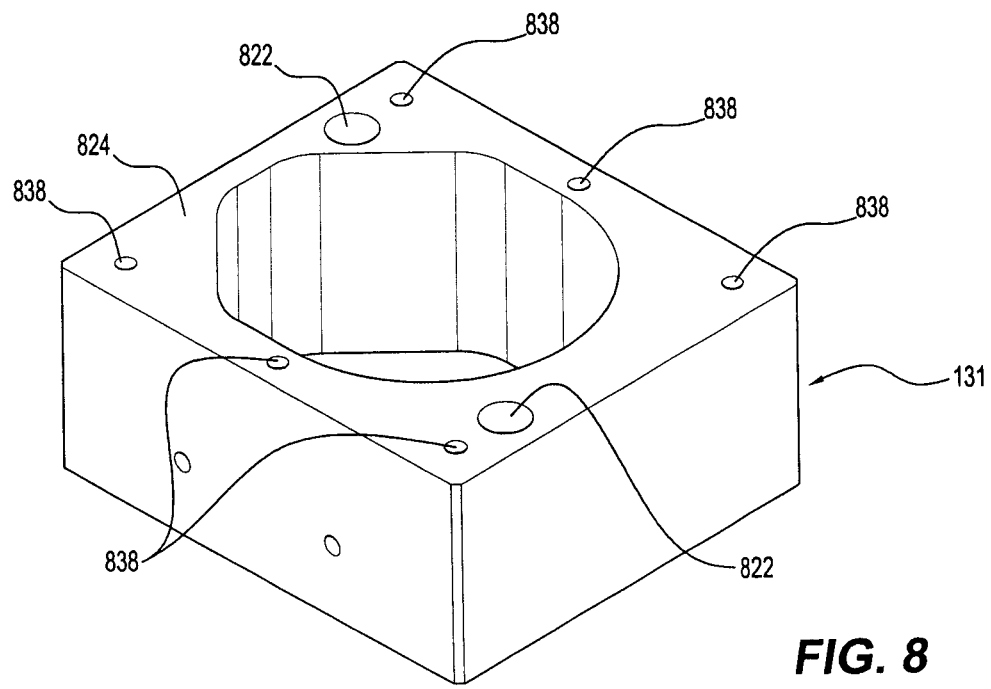
FIG. 8 is a top perspective view of a housing component of the upper part of the entry stage of the apparatus of FIG. 1.
Figure 9A:
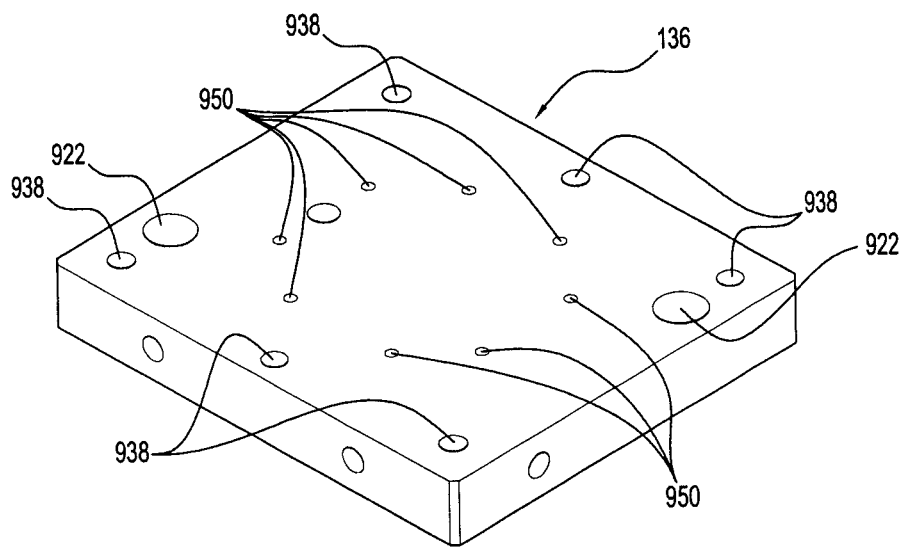
FIG. 9A is a perspective view of a top plate of the upper part of the entry stage of the apparatus of FIG. 1.
Figure 9D:
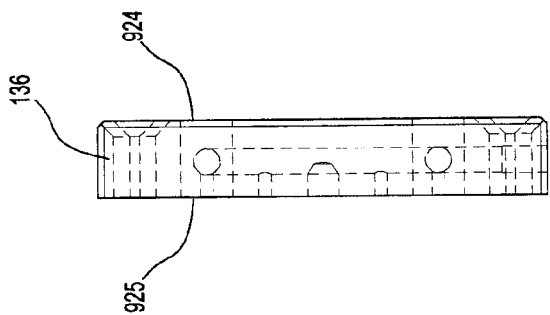
FIGS. 9C, 9D and 9E are first, second and third side views of the top plate of FIG. 9B.
Figure 9B:
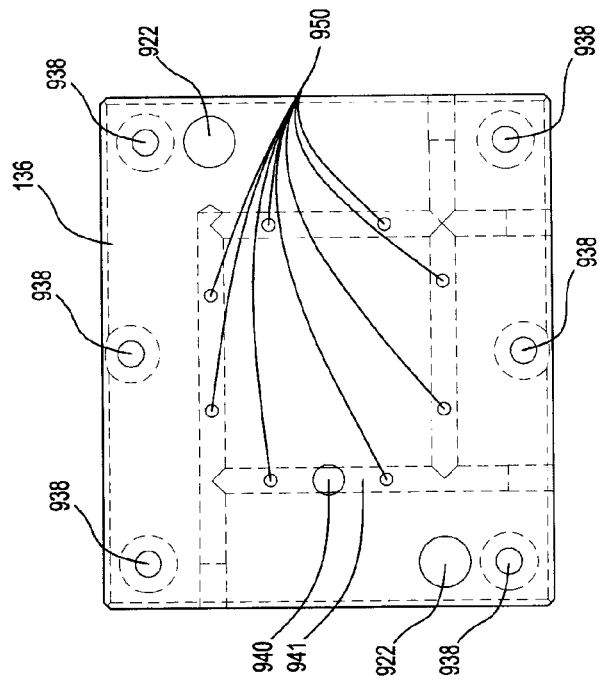
FIG. 9B is a plan view of the top plate of FIG. 9A.
Figure 9E:
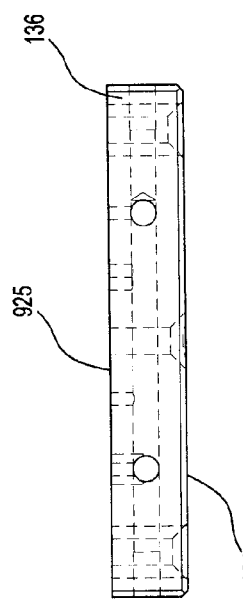
Figure 9C:
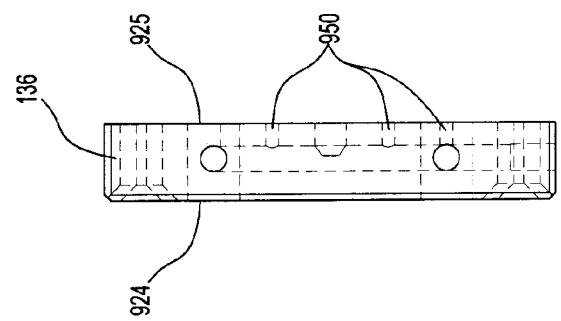

Referring now to FIGS. 7A to 7C, 8 and 9A to 9E, the upper part 130 of the entry stage 120 is described in further detail. This upper part 130 is interchangeable with the upper part 230 of the apparatus 200, as is described in further detail below. Upper part 130 has one part 149b of the hinge 149 coupled to one side of the housing component 131 for mating with the other hinge component 149a when upper part 130 is mounted to lower part 140. As shown in FIG. 8, housing component 131 has fastener receiving apertures 822 through which the shaft of screw-threaded fasteners 132 pass for engagement in apertures 622. Similarly, top plate 136 has fastener receiving apertures 922 to be aligned with the fastener receiving apertures 822. Housing component 131 and top plate 136 similarly have corresponding screw holes 838 and 938 around their periphery to receive screws 138 to affix the top plate 136 to the housing component 131 in a tight sealing manner.

Top plate 136 has an upper surface 924 and an opposed lower surface 925 and has at least one bore formed therein to act as an air conduit 941 between the air supply conduit 122 and the air delivery nozzle 134. In this respect, air delivery nozzle 134 is coupled to an outlet 940 of the fluid passage formed in top plate 136. Opening 940 is formed in the lower surface 925 of the top plate 136, which defines an upper wall of the entry chamber 610. As shown best in FIG. 9B, top plate 136 may also define a set of passages in communication with air conduit 941 and having a ring of air outlets 950 defined by and formed in the top plate 136. The passages and air conduit 941 effectively form a ring main to convey the compressed air to the nozzle 134 and small apertures 950 drilled into the ring main. These eight small holes (shown in FIG. 9B) provide a curtain of downward flowing air to avoid or minimise particles being inadvertently transported up into the entry stage. Thus, in addition to the nozzle air, there is air flowing down the small air outlets 950 to keep air and particulate movement heading in the right direction.

Figure 2:
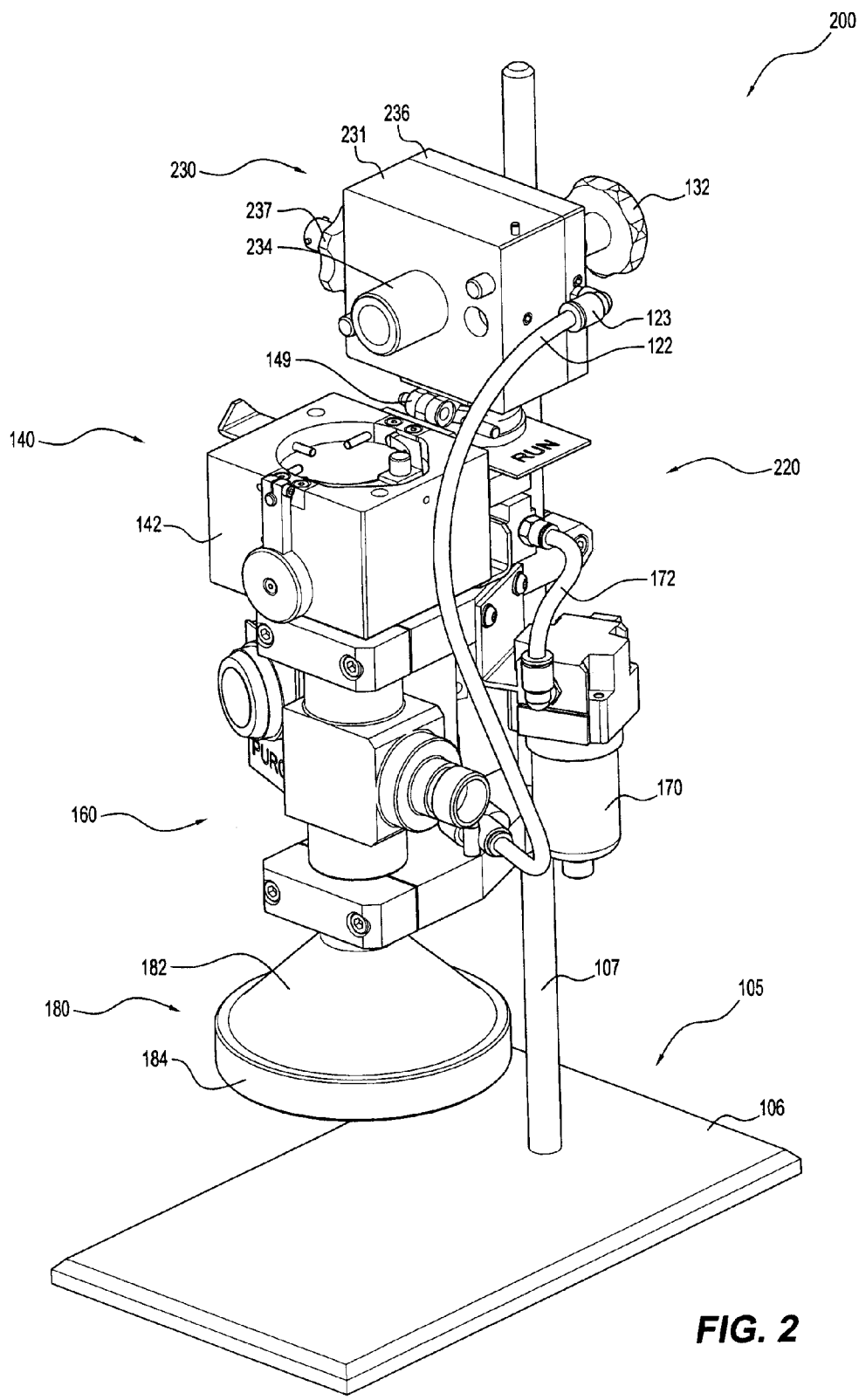
FIG. 2 is a perspective view of apparatus according to further embodiments for particulate detection.

Referring now to FIG. 2, an apparatus 200 is shown, which is identical to the apparatus 100, except for its use of a modified upper part 230 of entry stage 220. Upper part 230 is specifically configured to receive a magnetic chip holder 237 having ferrous particles held magnetically on an annular magnet 1035 (FIG. 10E) positioned toward a tip thereof, as an alternative to using the filter membrane 125 as the element that supports the particulate matter to be passed through the sensor 160. Thus, entry stage 220 comprises a modified upper part 230, but has the same lower part 140 as entry stage 120 in apparatus 100.

In some embodiments, the apparatus 100/200 may be provided for use in the form of a kit having interchangeable upper parts 130 and 230, each being substitutable for the other, depending on whether it is desired to analyse particulate on a filter membrane such as a filter patch, or ferrous particulate on a magnetic chip holder. If upper part 230 is used, then membrane clamp 146 is superfluous.

Because apparatus 200 uses exactly the same lower part 140, sensor 160 and recovery stage 180 (and interacts with computer 1420 in the same way) as apparatus 100, only the difference in the upper part 230 will be described in relation to apparatus 200. FIGS. 10A to 10E, 11A to 11E and 12A to 12E illustrate the parts of the upper part 230 in further detail.

Upper part 230 has a housing component 231 to which a top plate 236 is affixed by screws 138.

Figure 10A:
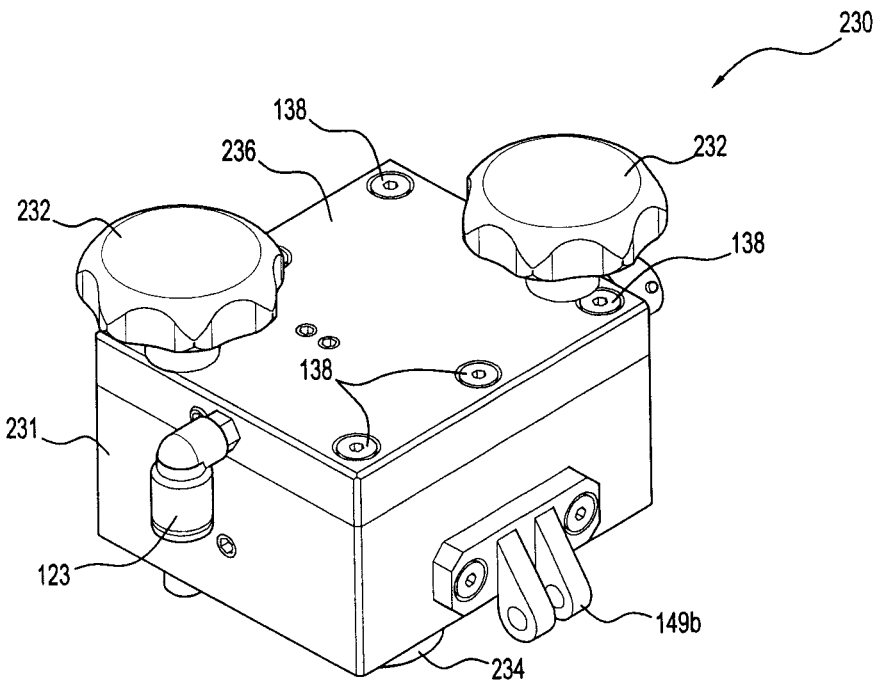
FIG. 10A is a top perspective view of an upper part of the entry stage of the apparatus shown in FIG. 2.
Figure 10E:
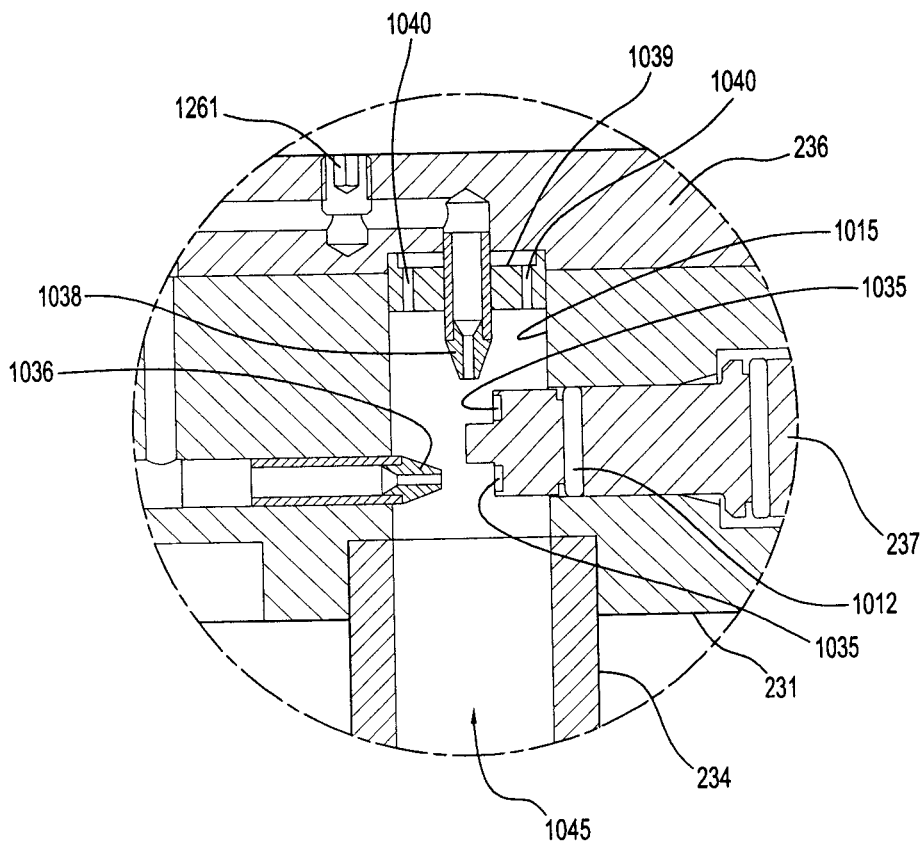
FIG. 10E is a magnified view of part of the upper part of the entry stage shown in FIG. 10D, as indicated by section D.
Figure 10B:
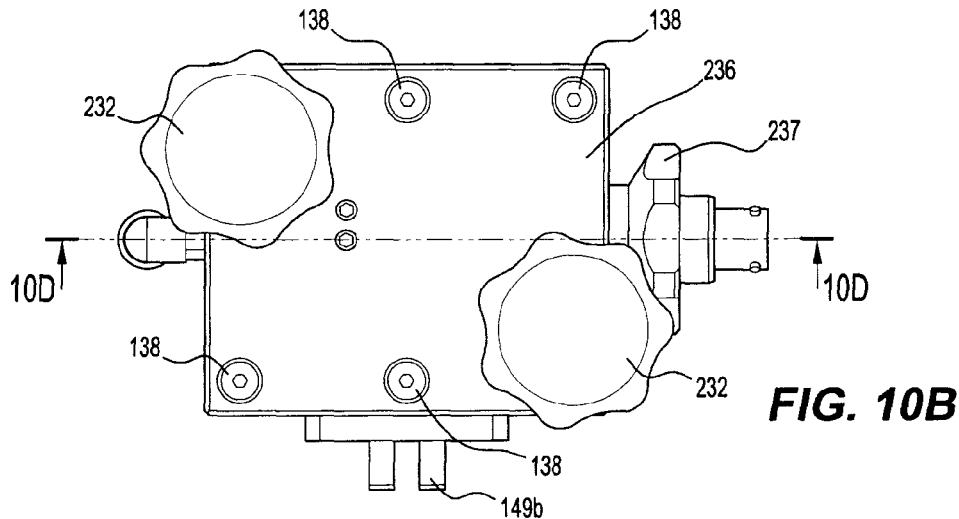
FIG. 10B is a plan view of the upper part of the entry stage shown in FIG. 10A.
Figure 10C:
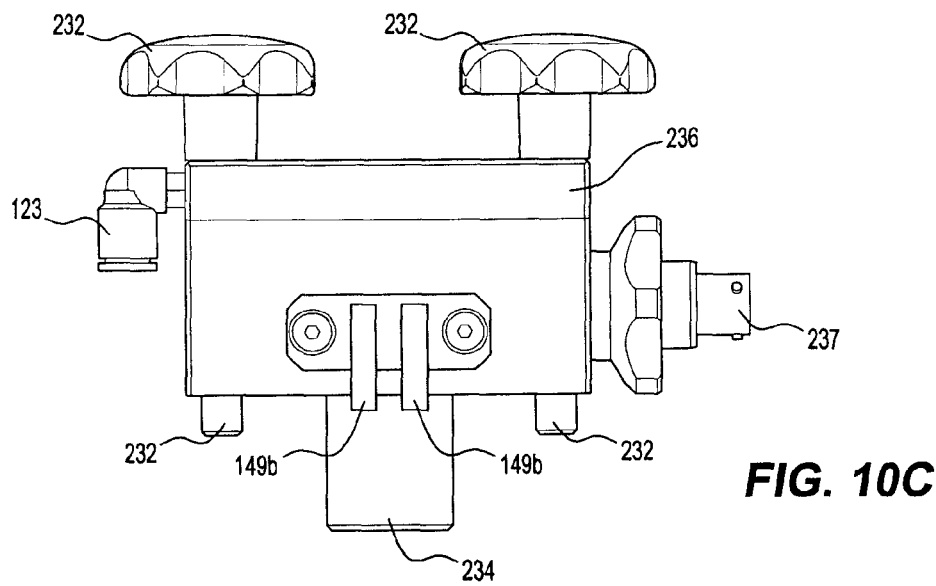
FIG. 10C is a side view of the upper part of the entry stage shown in FIG. 10A.
Figure 10D:
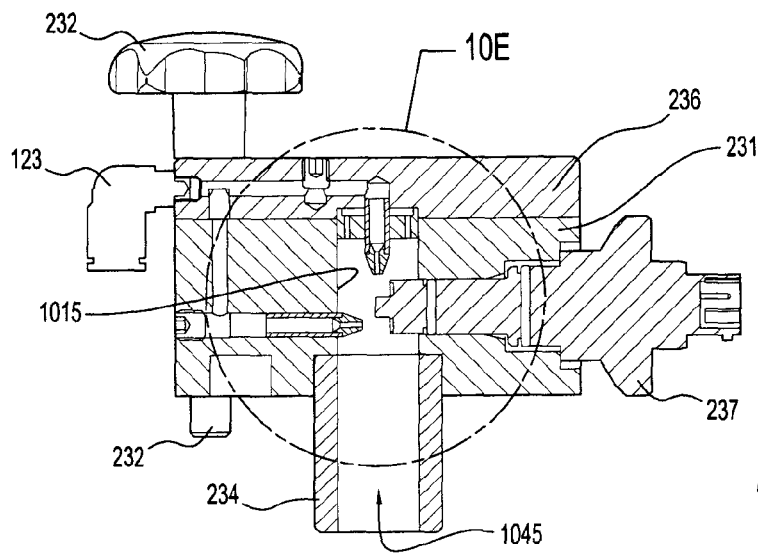
FIG. 10D is a side cross-sectional view of the upper part of the entry stage, taken along line A-A of FIG. 10B.

As is best illustrated in FIG. 10E, housing component 231 has an interior wall surface 1015 defining an upper part of the entry chamber 610 and a particulate delivery conduit 234 extending from a bottom portion of the housing component 231 to be received within that part of entry chamber 610 defined by the lower part 140 when the entry stage 220 is in its closed position. As shown in FIG. 10E, housing component 231 accommodates a horizontal nozzle 1036 and a vertical nozzle 1038, both of which are directed to impinge pressurised air on the magnetic tip 1035 of the magnetic chip holder 237 in order to dislodge particulate therefrom. The horizontal nozzle 1036 is offset from the longitudinal (axial) centreline of the magnetic chip holder 237 so that the jet of high velocity air from horizontal nozzle 1036 impinges on part of the annular magnet 1035 that has captured the particulate. Manual rotation of the magnetic chip holder 237 ensures that the air from the horizontal nozzle 1036 nozzle impinges on the entire annulus of magnet 1035, thus tending to remove the ferromagnetic particulate retained on magnet 1035. The vertical nozzle 1038 provides a means for ensuring the particles are entrained and accelerated down to the sensor 160.

This arrangement is suitable for indicating magnetic chip detectors that are used in oil lines in aircraft since the accumulation of sufficient ferromagnetic debris on the annular magnet completes an electrical circuit and hence provides an indication to the aircraft pilot or ground crew. Once such a magnetic chip detectors (holders) is removed from the aircraft machinery, it can be inserted into upper part 230 and the particulate retained thereon quantised in the manner described.

Coaxial to the vertical nozzle is a ring of compressed air outlets 1040 that provide a low velocity curtain of downward flowing air to ensure particles are not inadvertently trapped in the upper portion of the chamber. Some other designs of magnetic chip holder tend to retain the particles on a centreline magnet and would require a modified housing component 231 with no offset of the horizontal nozzle 1036; the top plate 236 would remain unchanged for such designs.

The horizontal and vertical nozzle 1036, 1038 are fixed in position by either or both of the housing component 231 and top plate 236. In the illustrated embodiments, vertical nozzle 1038 is held in position by bushing 1039 extending at least partly within chamber wall 1015 and partly received in a recess 1239 formed in the top plate 236. The bushing also defines the ring of air outlets 1040. Horizontal nozzle 1036 is positioned within a passage defined by the housing component 231, with the outlet end of the horizontal nozzle 1036 protruding into the upper part of the entry chamber 610 defined by chamber wall 1015.

Horizontal nozzle 1036 and vertical nozzle 1038 both receive pressurised air from the same source via conduit 122. This pressurised air is communicated to nozzles 1036, 1038 by fluid transmission passages formed within the top plate 236 and/or housing component 231.

Magnetic chip holder 237 has an internal sealing member 1012 to be positioned inside housing component 231, and optionally one or more further sealing members. A barrel of the magnetic chip holder 237 can thus be inserted and sealingly retained within a chip holder receiving aperture 1137 defined by an inner wall 1138 of the housing component. The magnetic chip holder 237 may have screw threads that engage with complementary screw threads formed in inner wall 1138 in order to assist in manually inserting and retaining the magnetic chip holder 237 in position within upper part 230.

Figure 11A:
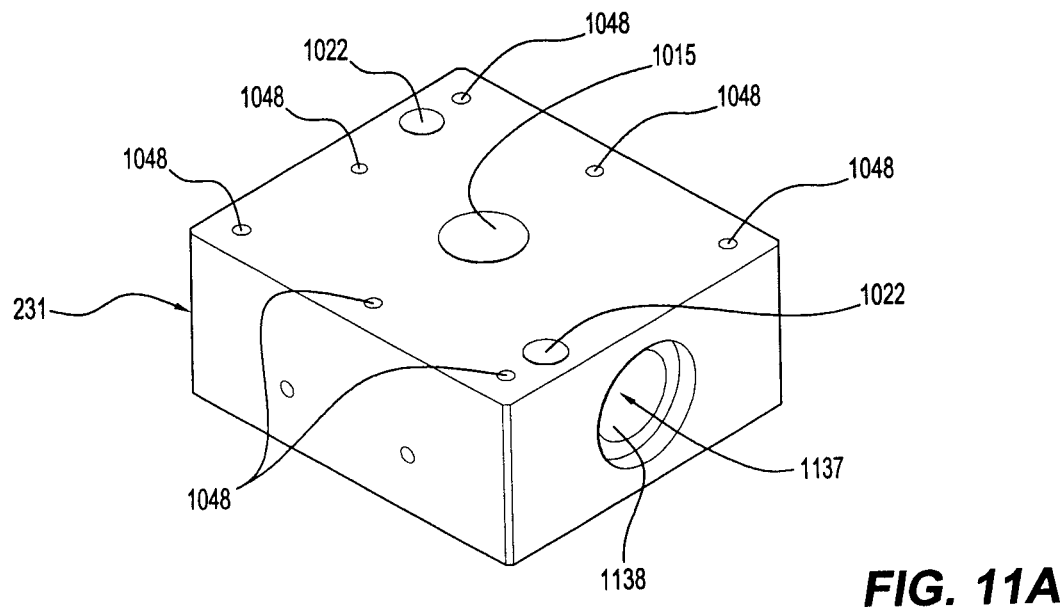
FIG. 11A is a perspective view of a housing component of the upper part of the entry stage shown in FIG. 10A.
Figure 12A:
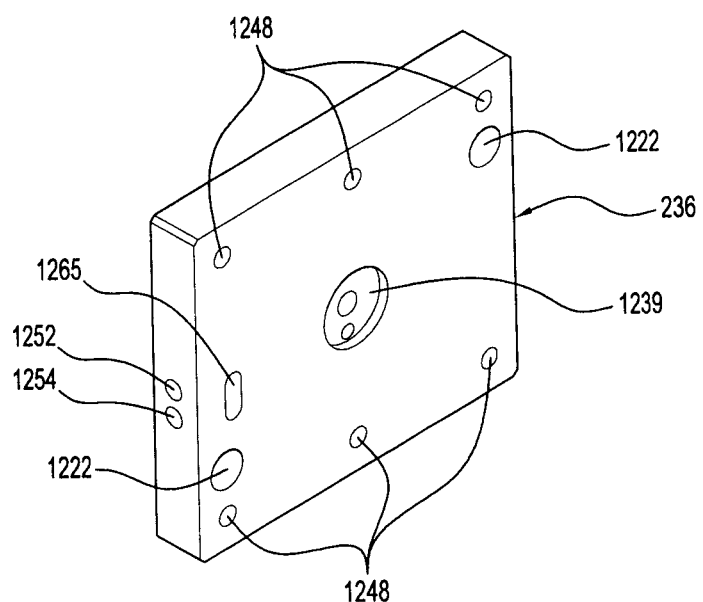
FIG. 12A is a perspective view of a top plate of the upper part of the entry stage of the apparatus shown in FIG. 2.
Figure 11E:
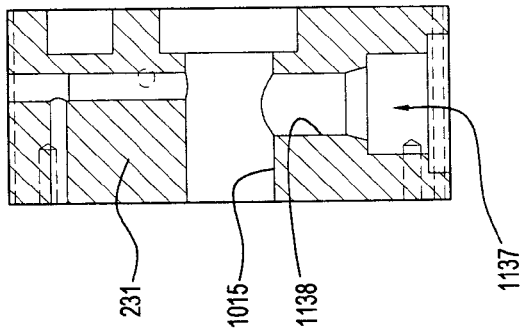
FIG. 11E is a side cross-sectional view of the housing component of FIG. 11A, taken along line D-D of FIG. 11B.
Figure 11B:
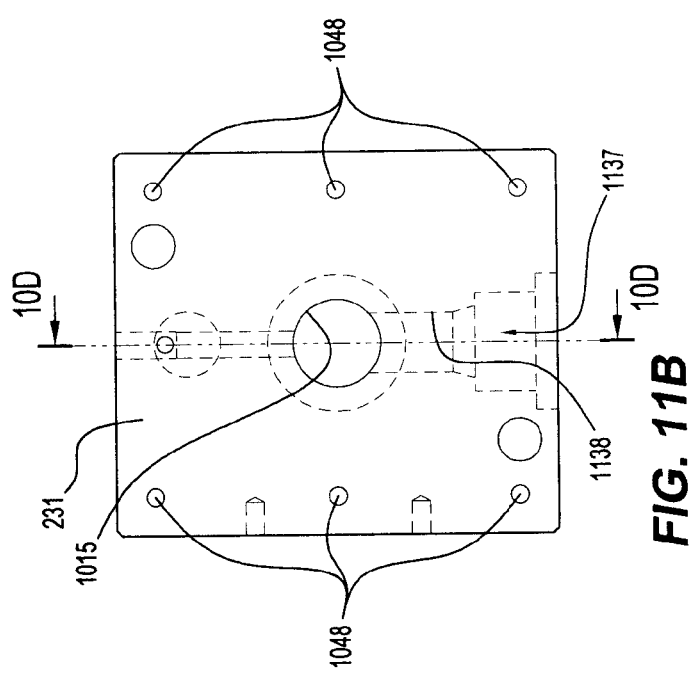
FIG. 11B is a plan view of the housing component of FIG. 11A.
Figure 11D:
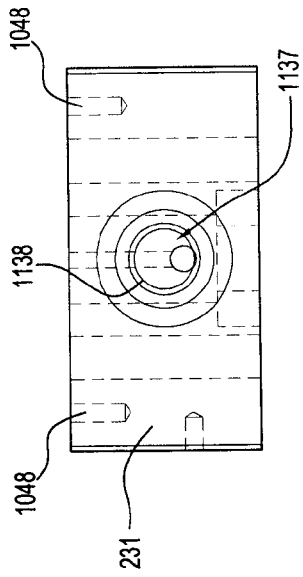
FIGS. 11C and 11D are first and second side views of the housing component of FIG. 11B.
Figure 11C:
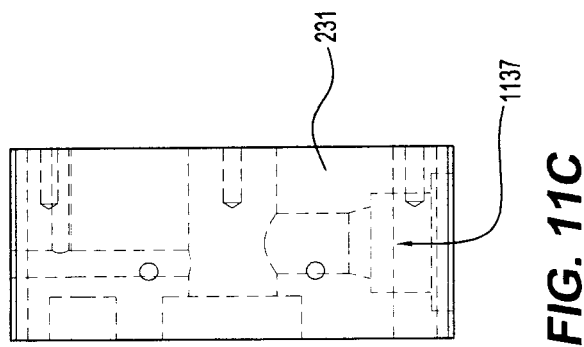
Figure 12D:
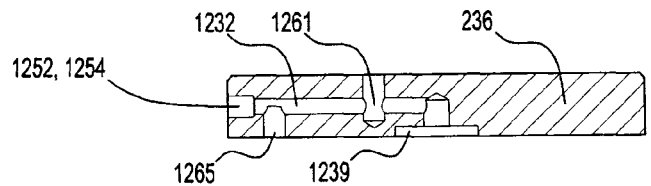
FIG. 12D is a cross-sectional view of the top plate of FIG. 12B, taken along line E-E of FIG. 12B.
Figure 12E:
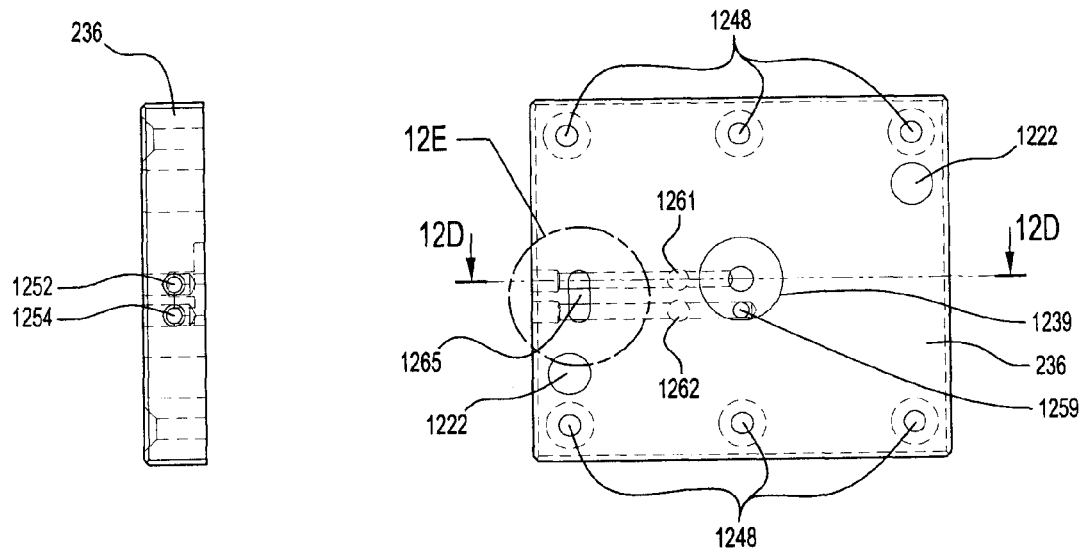
FIG. 12E is a magnified view of part of the top plate of FIG. 12B shown as section F in FIG. 12B.
Figure 12E:
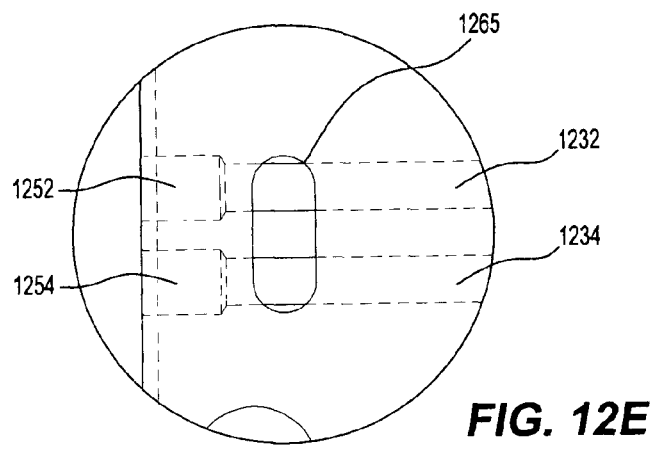

As shown in FIGS. 11A and 12A, the housing component 231 and the top plate 236 have complementary fastener-receiving apertures 1022 and 1222 for receiving the shaft of screw-threaded fasteners 232. Additionally, housing component 231 and top plate 236 have complementary screw holes 1046, 1246 for receiving screws 138 to securely fasten them together.

Compressed air is conveyed to the vertical nozzle 1038 via one of first and second entry holes 1252, 1254 (the other of which is blocked off after initial formation), as shown in FIG. 12C. A first air passage 1232 defined by the top plate 236 conveys compressed air to the vertical nozzle 1038. A second air passage 1243 defined by the top plate 236 conveys compressed air to the ring of holes 1040 formed in bushing 1039 that provide the downward curtain of air into the entry chamber. A horizontal nozzle supply slot 1265 provides communication of pressurised air from the inlet (i.e. via one of holes 1252, 1254) to the horizontal nozzle 1036 via a conduit formed in the housing component 231. First and second air flow control screw holes 1261, 1262 are formed in top plate 236 to receive grub screws that are used to allow manual flow control adjustment of air to the vertical nozzle 1038 and ring of holes 1040.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

PARTS LIST

100/200 apparatus for particulate detection
105 retort stand
106 base
107 post
111 upper support clamp
112 lower support clamp
114 run button
116 purge button
120/220 entry stage
122 air supply conduit
123 conduit coupling
125 filter membrane
130/230 upper part of the entry stage
131/231 housing component
132/232 fastener
134 air delivery nozzle
136/236 top plate
138 screws
140 particulate receiver/lower part of entry stage
141 coupling nozzle
141a shoulder
142 receiver body
143 bearing seat
144 membrane positioning lever
145 outlet passage
146 membrane clamp
147 membrane supports
148 clamp screw 149a,b lid coupling hinge
160 particulate sensor
161 sensor body
162 inlet port
163 outlet port
165 passage
168 sensor coupling
170 air filter
171 filter inlet
172 air supply conduit
180 recovery stage
182 conical body
184 recovery cap
185 circumferential lip/flange
186 coupling nozzle
187 recovery passage
188 shoulder
190 air supply valve
234 delivery conduit
237 magnetic chip holder
311 inlet sealing member
312 outlet sealing member
348 spring member
400 pneumatic control components
414 run valve
416 purge valve
510 porous grate
512 central magnet
520 recovery membrane
610 input chamber
612 clamp seat positioning notches
615 chamber wall surface
622 fastener receiving apertures
624 upper surface of receiver body
626 chamber upper rim
822/922 fastener receiving apertures
824 housing component upper surface
838/938 screw holes
924 top plate upper surface
925 top plate lower surface
941 air supply conduit
950 air curtain air supply passage
1012 internal sealing member
1015 chamber wall surface
1022 fastener receiving apertures
1035 magnetic tip
1036 horizontal nozzle
1038 vertical nozzle
1039 bushing
1040 air curtain air supply passage
1045 delivery passage
1048 screw holes
1137 chip holder receiving aperture
1138 inner wall surface
1222 fastener receiving apertures
1232 vertical nozzle air supply passage
1234 air curtain air supply passage
1239 recess (for bushing 1039)
1248 screw holes
1252 first entry aperture
1254 second entry aperture
1259 air curtain supply aperture
1261 first flow control screw hole
1262 second flow control screw hole
1265 horizontal nozzle supply slot
1311 first bearing arm
1312 second bearing arm
1320 central body
1348 clamp screw hole
1349 clamp screw fixed nut
1351 membrane support flange
1352 concave rim
1400 system for particulate quantisation
1410 source of pressurised air
1420 computer
1430 memory
1435 signal processing module
1438 signal processing component
1440 processor
1450 display The claims defining the invention are as follows:

1. Apparatus for metallic particulate detection, comprising:
an entry stage defining an input chamber to receive an element having particulate matter thereon;
a sensor defining a passage in fluid communication with the input chamber to receive the particulate matter from the input chamber and to detect the particles in the particulate matter;
a vented recovery stage defining a recovery chamber to receive and capture at least some of the particulate matter passing through the passage; and
at least one air outlet positioned in the input chamber to direct pressurised air from the at least one air outlet to impinge on the element to remove the particulate matter from the element.

2. The apparatus of claim 1, further comprising a source of pressurised air coupled to the at least one air outlet.

3. The apparatus of claim 1, further comprising a filter to filter air from the pressurised air source.

4. The apparatus of claim 1, wherein the recovery stage comprises a porous grate to allow venting of the air.

5. The apparatus of claim 4, wherein a porous membrane is positionable, in use of the apparatus, on the grate to retain the particulate matter in the recovery stage as the air is vented.

6. The apparatus of claim 4, wherein the grate is manually removable from the recovery stage.

7. The apparatus of claim 4, wherein the grate has a centrally located magnet to attract ferromagnetic particulates.

8. The apparatus of claim 1, wherein the recovery chamber has a larger cross-sectional area than the passage, the recovery chamber widening in a direction of travel of the air.

9. The apparatus of claim 1, wherein the apparatus is sized to be supported by a retort stand.

10. The apparatus of claim 1, wherein the at least one air outlet comprises at least two air outlets.

11. The apparatus of claim 1, wherein the sensor is configured to detect particles of the particulate matter greater than or equal to about 100 microns.

12. The apparatus of claim 1, wherein the element is a filter membrane.

13. The apparatus of claim 12, wherein the entry stage comprises a clamp to hold an edge of the filter membrane.

14. The apparatus of claim 13, wherein the clamp is movable within the input chamber to facilitate separation of particulate matter from the filter membrane.

15. The apparatus of claim 14, wherein the clamp is rotatable between a first position and a second position, and wherein, in the first position, the filter membrane is generally horizontal and supports any particulate matter thereon, and in the second position, the clamp allows the filter membrane to be freely suspended within the input chamber.

16. The apparatus of claim 1, wherein the element comprises a magnet to attract ferromagnetic matter.

17. The apparatus of claim 16, wherein the at least one air outlet comprises multiple air outlets each arranged to direct air toward the magnet from a different direction.

18. The apparatus of claim 17, wherein the input stage has a wall defining an opening therein to receive a magnet support element to which the magnet is coupled.

19. The apparatus of claim 1, wherein the entry stage, the sensor and the recovery stage are substantially co-axial.

20. A metallic particulate quantisation system comprising:
   the apparatus of claim 1; and
   a computer coupled to receive an output of the sensor and configured to detect a size and quantity of particles in the particulate matter passing through the sensor passage based on the sensor output.

* * * * *